(12) United States Patent
Behan

(10) Patent No.: US 6,942,630 B2
(45) Date of Patent: Sep. 13, 2005

(54) INFLATABLE SUSPENSION HARNESS/BODY JACKET

(75) Inventor: Edward Behan, Blue Point, NY (US)

(73) Assignee: Biodex Medical Systems, Inc., Shirley, NY (US)

( * ) Notice: Subject to any disclaimer, the term of this patent is extended or adjusted under 35 U.S.C. 154(b) by 548 days.

(21) Appl. No.: 10/124,531

(22) Filed: Apr. 16, 2002

(65) Prior Publication Data

US 2003/0195445 A1 Oct. 16, 2003

(51) Int. Cl.[7] .................................................. A61F 5/00
(52) U.S. Cl. ............................ 602/19; 602/13; 602/32; 128/875; 482/69
(58) Field of Search ............................... 602/13, 19, 32, 602/36; 128/869, 870, 873–875; 2/456; 482/43, 66, 69

(56) References Cited

U.S. PATENT DOCUMENTS

| | | | |
|---|---|---|---|
| 560,165 A | 5/1896 | Heckler | |
| 682,160 A | 9/1901 | Anderson | |
| 961,282 A | 1/1910 | Badger | |
| 1,164,312 A | 12/1915 | Morton | |
| 1,452,411 A | 4/1923 | Bunn | |
| 1,704,550 A | 3/1929 | Brygider | |
| 1,792,125 A | 2/1931 | Shave | |
| 2,114,301 A | 4/1938 | Harrigan | |
| 2,393,285 A | 1/1946 | Brown | |
| 3,424,134 A | * 1/1969 | Rosenblum | 182/3 |
| 4,047,255 A | 9/1977 | Kiefer | |
| 4,496,328 A | 1/1985 | Asher | |
| 4,512,437 A | * 4/1985 | Savage | 182/3 |
| 4,534,341 A | 8/1985 | Bart et al. | |
| 4,722,329 A | * 2/1988 | Kalvag | 602/32 |
| 4,913,589 A | 4/1990 | Faulconer | |
| 4,981,307 A | 1/1991 | Walsh | |
| 4,990,115 A | 2/1991 | Vorhauer | |
| 5,346,419 A | 9/1994 | Kaiser | |
| 5,378,084 A | 1/1995 | Walters et al. | |
| 5,385,496 A | 1/1995 | Seligman | |
| 5,451,121 A | 9/1995 | Seligman | |
| 5,498,219 A | 3/1996 | Soufi | |
| 5,502,851 A | * 4/1996 | Costello | 5/86.1 |
| 5,562,513 A | 10/1996 | Kaiser | |
| 5,662,433 A | 9/1997 | Seligman | |
| 5,662,560 A | 9/1997 | Svendsen et al. | |
| 5,695,432 A | 12/1997 | Soderlund | |
| 5,759,076 A | 6/1998 | Bateman et al. | |
| 6,120,213 A | 9/2000 | Stinton | |
| 6,125,792 A | 10/2000 | Gee | |
| 6,135,928 A | 10/2000 | Butterfield | |
| 6,139,475 A | * 10/2000 | Bessler et al. | 482/69 |
| 6,146,315 A | 11/2000 | Schonenberger | |
| 6,273,844 B1 | 8/2001 | Kelsey et al. | |
| 6,315,138 B1 | 11/2001 | Dyson | |
| 6,436,011 B1 | * 8/2002 | Cook | 482/69 |
| 6,578,594 B1 | * 6/2003 | Bowen et al. | 135/67 |
| 6,698,026 B2 | * 3/2004 | Schweer | 2/94 |
| 6,752,776 B2 | * 6/2004 | West | 602/36 |
| 6,824,106 B2 | * 11/2004 | Douglas et al. | 244/151 R |

* cited by examiner

Primary Examiner—Henry Bennett
Assistant Examiner—Amanda Wieker
(74) Attorney, Agent, or Firm—Gibbons, Del Deo, Dolan, Griffinger & Vecchione

(57) ABSTRACT

An inflatable suspension harness/body jacket and method of use in medical partial weight-bearing therapy. The suspension harness/body jacket is fit onto a patient and has bladders that are inflated sufficiently to achieve a tight conforming fit. Deflating and re-inflating the bladders where necessary to re-achieve the tight conforming fit allows for successful weight-bearing therapy without discontinuing the therapy for an extended period or removing the patient. The suspension harness/body jacket has shoulder straps and jacket portions that may pass through D-rings that, when attached to a frame or other apparatus, provide additional offloading capacity.

8 Claims, 5 Drawing Sheets

FIG.1

INFLATABLE SUSPENSION HARNESS/BODY JACKET

BACKGROUND OF THE INVENTION

1. Field of the Invention

The present invention is directed to an inflatable suspension harness/body jacket for use in medical applications, and especially is directed to an inflatable suspension harness/body jacket for use in medical partial weight-bearing therapy, where the jacket can be inflated to provide a tight, conforming fit to the wearer. The harness/body jacket is useful in a variety of medical applications, including alleviating conditions which may give rise to decubitus ulcers, or "pressure sores," in persons confined to a wheelchair, assisting medical personnel in the handling and treatment of incapacitated persons, and aiding incapacitated persons (including, without limitation, hemiplegic and paraplegic persons) during therapy and recovery.

2. Discussion of the Related Art

Partial weight-bearing therapy is a common means of rehabilitation for patients afflicted by stroke, spinal cord injury, joint replacement, back pain, obesity, arthritis, or amputation. The therapy generally involves lifting a patient by means of a harness to offload a determined amount of weight from the patient's lower extremities. The harness generally is integral to a vest that is fitted to the patient. To accommodate the variety of body types and sizes, current vest harnesses rely on cinching straps or compressive netting in conjunction with differently sized vests.

Unfortunately, these methods do not always accommodate differently-sized patients. Many patients find the vest harness to be uncomfortable because of the limitations in achieving a tight conforming fit, that is, a fit that closely follows the precise body plan of the individual patient, including vagaries of curvature. Without a tight conforming fit, however, the harness vest likely will slip and "ride up" on the patient. In addition to resulting in discomfort, such "riding up" could inhibit breathing and restrict circulation, possibly exacerbating the condition for which the patient is receiving partial weight-bearing therapy, in the first place.

Still further, in the present technology, any change in the tight conforming fit of the harness/vest resulting from the partial weight-bearing therapy itself requires temporarily halting the therapy, disengaging the patient from any apparatus associated therewith (to which the harness is attached), and readjusting the fit of the harness/vest. That is, where the harness/vest loses its initial tight conforming fit as a result of the movements of the patient during therapy, the therapy must be discontinued, the patient disengaged from any apparatus, and either the cinching straps readjusted, or (particularly in the case of a compressive netting vest) the entire harness/vest replaced. This results, at the very least, in a discontinuity in the therapy. More likely, the benefits of the particular therapy session prior to the loss of fit are lost.

What is needed is a harness/body jacket (or vest) for use in partial weight-bearing therapy and other related medical applications, that can provide a tight conforming fit for differently-sized patients. What is further needed is a harness/body jacket (or vest) for use in partial weight-bearing therapy and other related medical applications, which allows for the tight conforming fit to be readjusted easily after the vest/harness has been placed on the patient, and the offloading has commenced, without requiring the therapy to be discontinued.

Accordingly, the present invention provides an inflatable suspension harness/body jacket for use in partial weight-bearing therapy and other related medical applications, that can provide a tight conforming fit for differently-sized patients. The present invention also provides an inflatable suspension harness/body jacket for use in partial weight-bearing therapy and other related medical applications, which allows for the tight conforming fit to be readjusted easily after the vest/harness has been placed on the patient, and the offloading has commenced, without requiring the therapy to be discontinued. The present invention also provides a method of using the inflatable suspension harness/body jacket to achieve the required tight conforming fit, and whereby the tight conforming fit can be re-achieved, where necessary, through re-inflation or deflation of the inflatable suspension harness/body jacket, without discontinuing the therapy for an extended period of time or removing the patient from the therapy apparatus.

BRIEF SUMMARY OF THE INVENTION

The inflatable suspension harness/body jacket of the present invention comprises a pair of shoulder straps, each having two ends; a jacket with a left jacket portion and a right jacket portion, each jacket portion having a front and a back, a top and a bottom, and inner and outer surfaces; at least one inflatable bladder secured to the inner surface of each of the left and right jacket portions; a plurality of thigh extension straps, each having two ends; and two thigh wraps (left and right), each wrap having a front and a rear. One end of each shoulder strap is secured to the top back of each jacket portion, with the other end being detachable from the top front of the same jacket portion. The shoulder straps are adjustable to fit varying body sizes.

The jacket is designed to be worn at the waist or lumbar level. The left and right jacket portions are attached to each other by means of a plurality of front straps secured to the front of each jacket portion, and a plurality of back straps secured to the back of each jacket portion. The front straps of the left jacket portion are removable from the corresponding front straps of the right jacket portion; and the back straps of the left jacket portion are removable from the corresponding back straps of the right jacket portion. Both the front straps and the back straps are adjustable by length to accommodate varying torso circumferences.

One end of at least one thigh extension strap is secured to the front of each of the left and right jacket portions, with the other end of each such thigh extension strap being secured to the front of one of the thigh wraps. Additionally, one end of at least one other thigh extension strap is secured to the back of each of the left and right jacket portions, with the other end of each such thigh extension strap being secured to the back of one of the thigh wraps. The thigh extension straps are adjustable by length to accommodate a variety of torso sizes. The thigh wraps, thigh extension straps and jacket portions are attached to each other so that the left thigh wrap is attached by a plurality of thigh extension straps to the left jacket portion, while the right thigh wrap is attached by another plurality of thigh extension straps to the right jacket portion.

Each of the inflatable bladders comprises two skins, attached to each other to form an inflatable hollow. The outer surface of one of the skins of each bladder is attached to the inner surface of the left or right jacket portion. Each of the inflatable bladders also comprises an inflation port for inflating the bladder. The inflation port includes an inflation regulating valve for regulating the inflating/deflating of the bladder. The inflation port may also include a hand pump for supplying air to inflate the bladder. Alternatively, the bladders may be inflated with gel or liquid or other gas.

Each of the shoulder straps passes through the central opening of a D-ring, prior to being attached to the front of the left or right jacket portion. The D-rings are configured so that, when the suspension harness/body jacket is worn, the shoulder strap D-rings may be attached to a frame or other apparatus for offloading a portion of a patient's body weight. In addition to the shoulder D-rings, each of the left and right jacket portions has a D-ring attached to the bottom thereof, at a point midway between the front and the back of the jacket portion. The jacket portion D-rings are configured so that, when the suspension harness/body jacket is worn, the jacket portion D-rings also may be attached to the frame or other apparatus, thereby providing additional offloading capacity.

The invention also discloses a method for achieving a tight conforming fit of the harness/body jacket. The harness/body jacket is placed on a patient. The jacket is initially fitted on the patient as follows: The shoulder straps are adjusted for fit. The jacket is adjusted for fit by adjusting the front and/or straps of the left and right jacket portions for length. The thigh extension straps are then adjusted for fit (by length), and the thigh wraps are adjusted for fit (by circumference). After the jacket is fitted initially, the bladders are inflated sufficiently to achieve the required tight conforming fit. In this manner, the jacket is able to conform the vagaries of body curvature and body type, and partial weight-bearing therapy may be conducted without fear of an unwanted shift in the fit of the harness/body jacket. Additionally, in the event that the tight conforming fit is lost during the course of the therapy, the bladders can be re-inflated or deflated, as necessary to re-achieve the tight conforming fit, without having to detach the patient from the frame or other therapy apparatus or interrupting the therapy for an extended period of time.

DETAILED DESCRIPTION OF THE INVENTION

Figure 1:
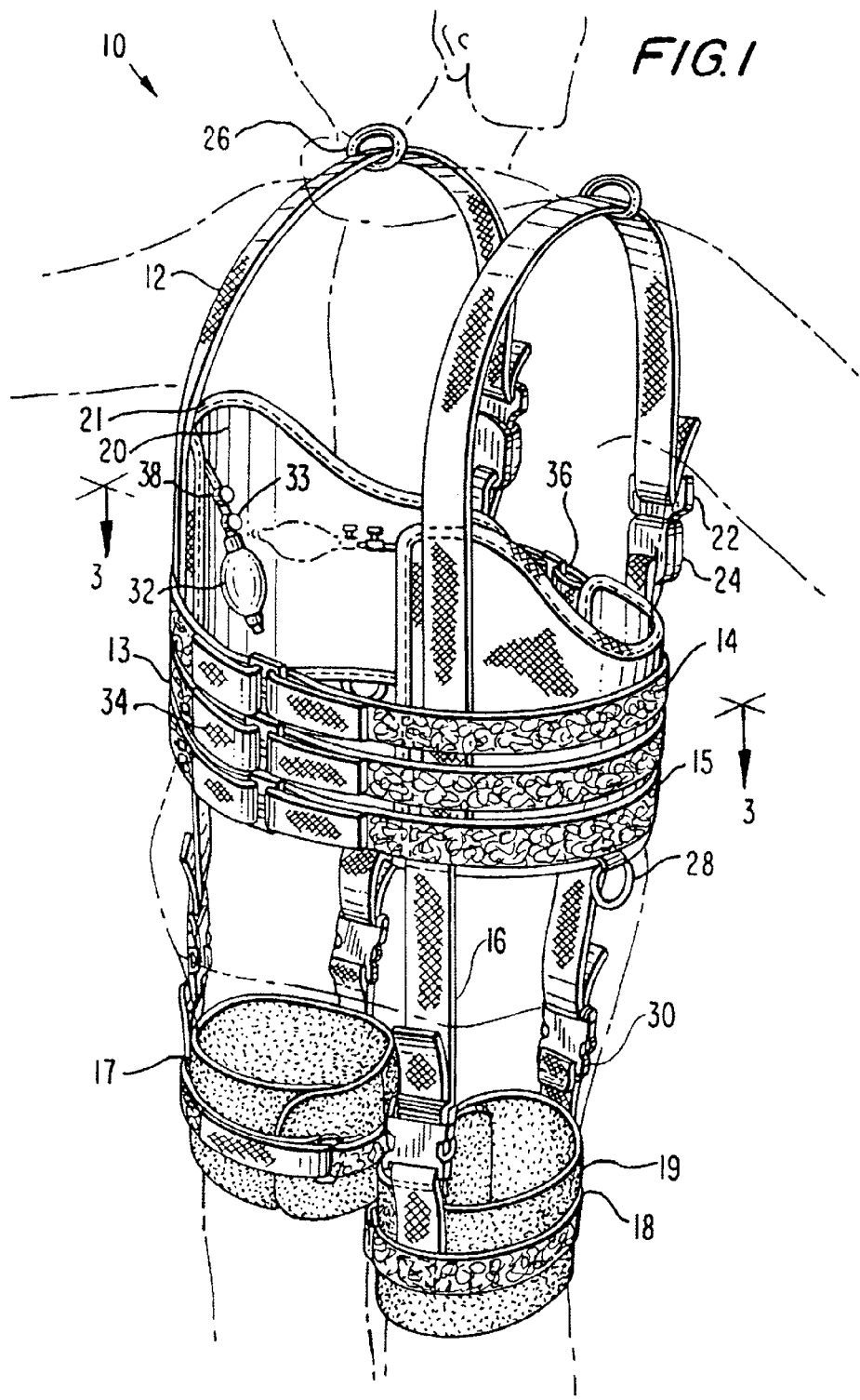
FIG. 1 shows a right rear perspective view of the inflatable suspension harness/body jacket of the present invention.
Figure 2:
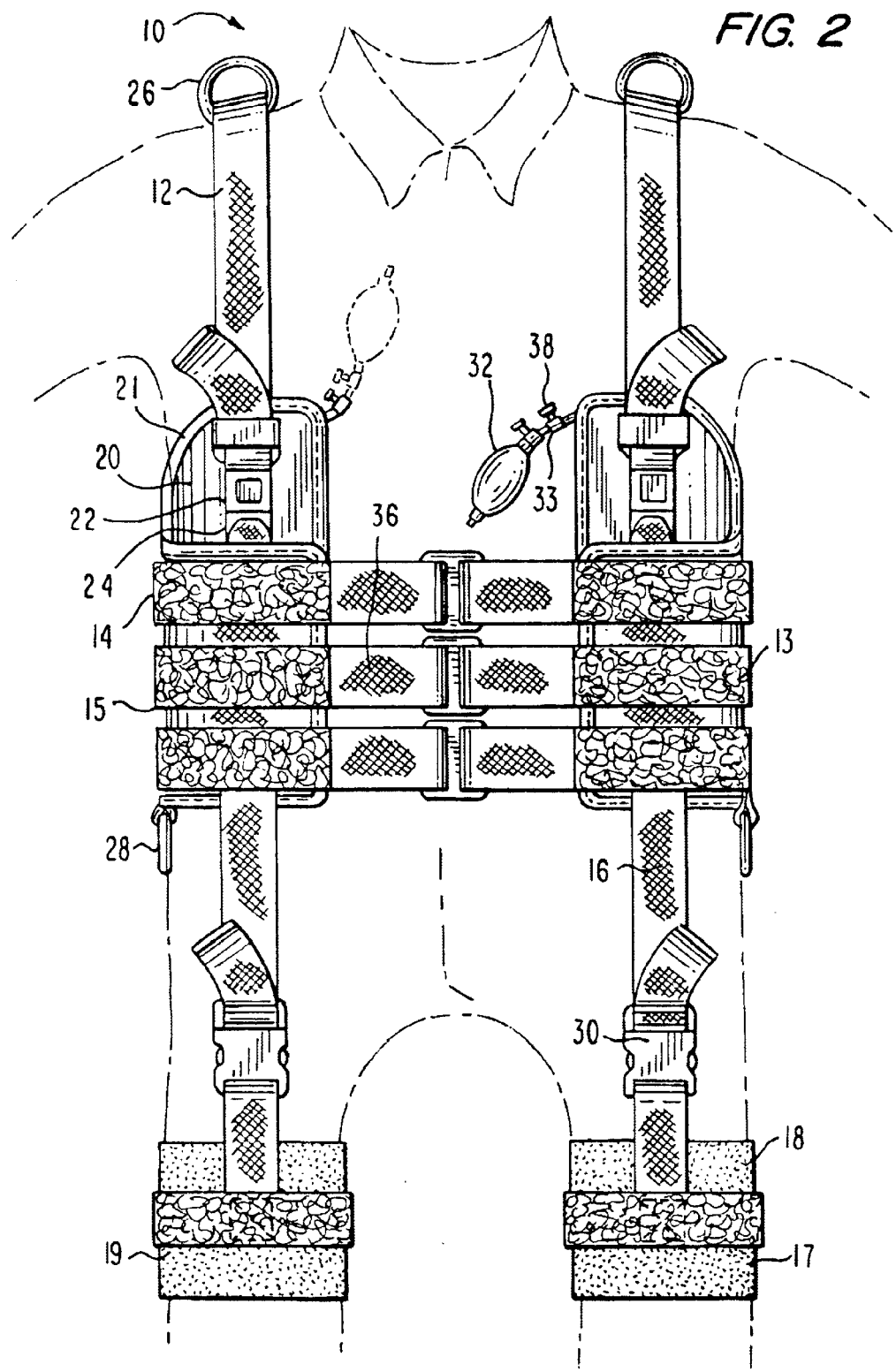
FIG. 2 shows a front view of the inflatable suspension harness/body jacket of the present invention.

Turning to FIGS. 1 and 2, the inflatable suspension harness/body jacket 10 of the present invention comprises two shoulder straps 12, each shoulder strap having two ends, one end of each shoulder strap passing through a central opening of a D-ring 26; a jacket 14 comprising a left jacket portion 13 and a right jacket portion 15, each jacket portion having a front and a back, a top and a bottom, and inner and outer surfaces, and having a further D-ring 28 securably attached to the bottom of the jacket portion at a point midway between the front and the back thereof; at least one inflatable bladder 20 securably attached to the inner surface of each of the left and right jacket portions 13, 15; a plurality of thigh extension straps 16, each strap having two ends; and two thigh wraps 18, corresponding to a left thigh wrap 17 and a right thigh wrap 19, each wrap having a front and a rear.

One end of each shoulder strap 12 is securably attached to the top back of each of the left and right jacket portions 13, 15, with the other end of the shoulder strap being detachably attached to the top front of the same jacket portion. The left and right jacket portions 13, 15 are attached to each other by means of a plurality of front straps 36 securably attached to the front of each jacket portion, and a plurality of back straps 34 securably attached to the back of each jacket portion. The front straps of the left jacket portion 13 are removably attached to the front straps of the right jacket portion 15, and the back straps of the left jacket portion 13 are removably attached to the back straps of the right jacket portion 15. The removable attachment may be by any conventional means, including, without limitation, Velcro®.

One end of at least one thigh extension strap 16 is securably attached to the front of each of the left and tight jacket portions 13, 15, the other end of each such thigh extension strap 16 being securably attached to the front of one of the thigh wraps 18. Similarly, one end of at least one other thigh extension strap 16 is securably attached to the back of each of the left and right jacket portions 13, 15, with the other end of each such thigh extension strap 16 being securably attached to the back of one of the thigh wraps 18.

The thigh wraps 18, thigh extension straps 16 and jacket portions 13, 15 are configured relative to each other such that the left thigh wrap 17 is attached by a plurality of thigh extension straps 16 to the left jacket portion 13, while the right thigh wrap 19 is attached by another plurality of thigh extension straps 16 to the right jacket portion 15. Each of the D-rings 26 through which the shoulder straps 12 pass is configured such that, when the suspension harness/body jacket 10 is worn, the D-rings 26 may be removably attached to a frame or other apparatus for offloading a portion of a patient's body weight. Each of the further D-rings 28 attached to the bottom of the left and right jacket portions 13, 15 is configured such that, when the suspension harness/body jacket 10 is worn, the further D-rings 28 also may be removably attached to the frame or other apparatus, thereby providing additional offloading capacity.

The detachable attachment of the shoulder straps 12 to the top front of the jacket portions 13, 15 may be by any conventional means. In a preferred embodiment, the detachable attachment is by a seatbelt-type clasp apparatus 22, 24. Additionally, the thigh extension straps 16 are configured to be adjustable in length, to accommodate patients of varying torso length. The adjustment configuration 30 may be by any conventional means.

Figure 3:
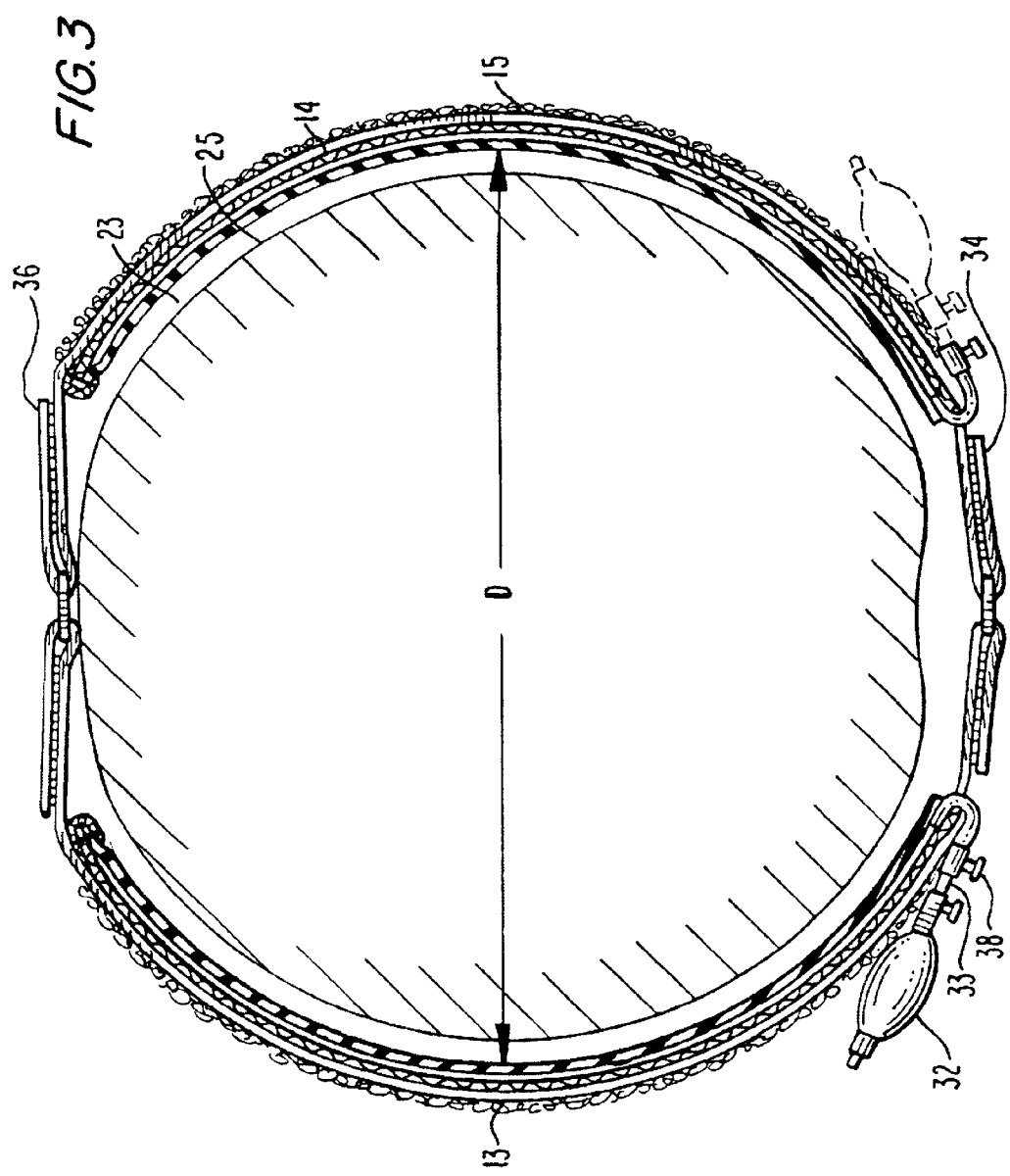
FIG. 3 shows a top cutaway view of the jacket portion of the inflatable suspension harness/body jacket of the present invention, showing the inflatable bladders as uninflated.
Figure 4:
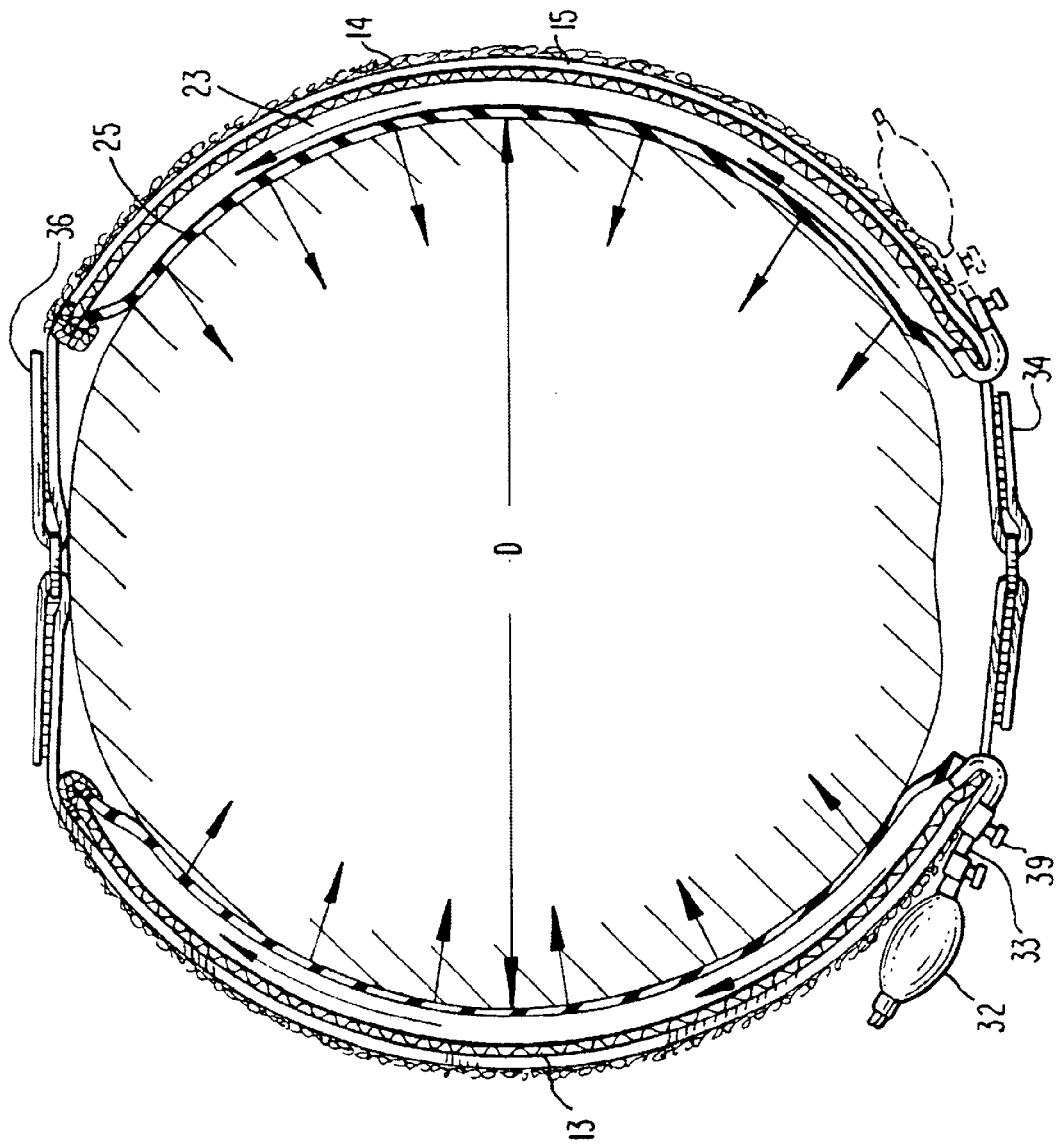
FIG. 4 is the same as FIG. 3, but with the inflatable bladders shown as inflated.
Figure 5:
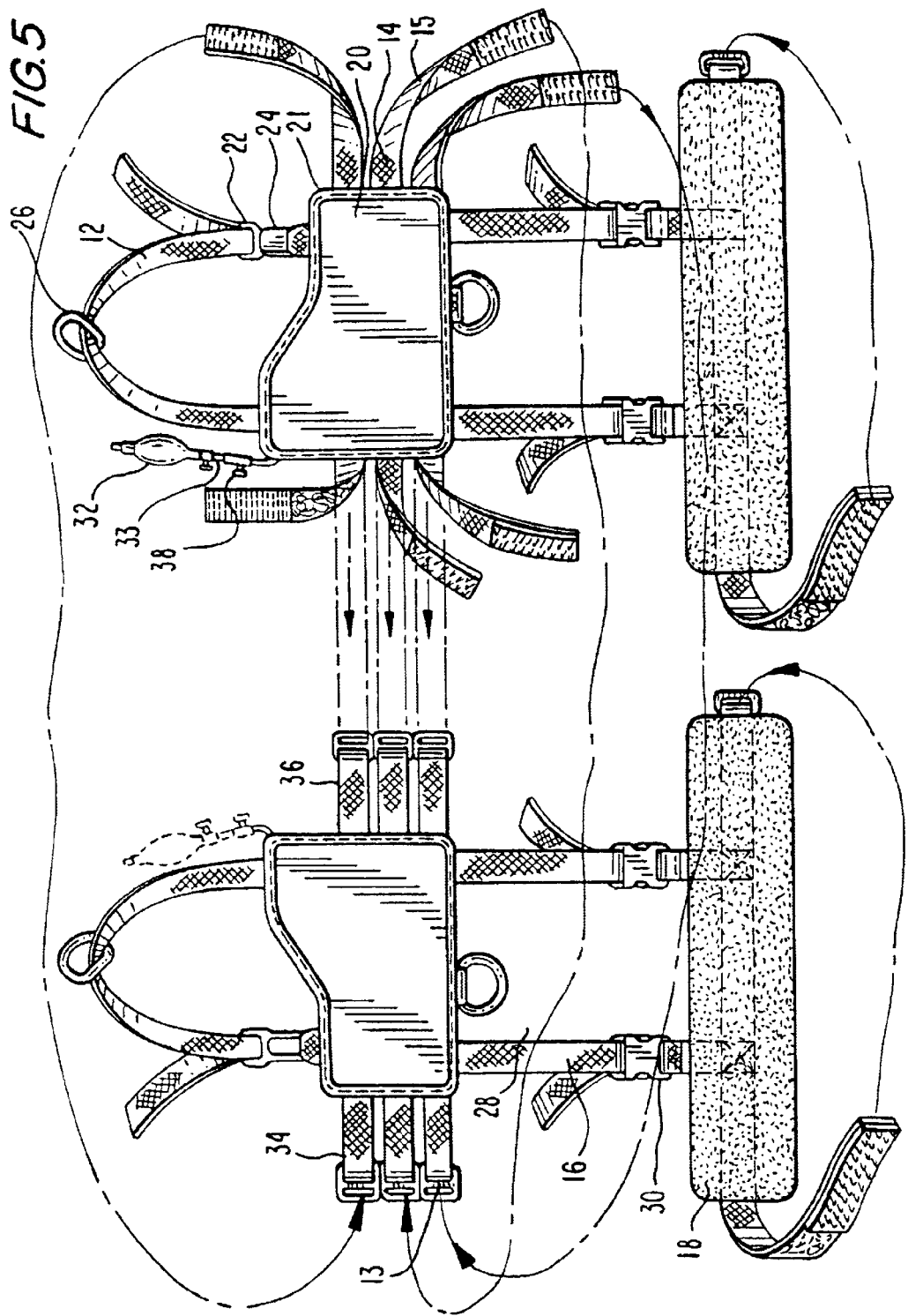
FIG. 5 shows an exploded front view of the inflatable suspension harness/body jacket of the present invention, with the harness/body jacket separated into left and right portions.

As shown in FIGS. 3 and 4, each of the inflatable bladders 20 further comprises two skins 25, each skin having an outer surface and an inner surface, and an edge. The skins 25 are securably attached to each other to form a hollow 23 described by the two inner surfaces. The outer surface of one of the skins 25 of each bladder 20 is securably attached to the inner surface of the left or right jacket portion, 13, 15. Each of the inflatable bladders 20 also includes an inflation port 33 for inflating the bladder, the inflation port 33 including an inflation regulating valve 38 for regulating the inflating and deflating of the bladder 20. In a preferred embodiment the inflation port 33 may include a hand pump 32 for supplying air to inflate the bladder 20 to achieve the required tight conforming fit. Alternatively, the bladders 20 may be inflated with gel or liquid or other gas.

The shoulder straps 12, jacket portions 13, 15, front and back straps 36, 34, thigh extension straps 16 and thigh wraps 30 may be made of conventional materials, such as nylon fabric. The bladders 20 (and the skins 25 thereof) also may be made of conventional materials, including rubber or rubberized fabrics. The D-rings 26 of the shoulder straps 12 and the further D-rings 28 of the left and right jacket portions 13, 15 may be made from any substance able to withstand the stress from the partially offloaded weight of a patient when the D-rings are attached to the offloading frame or apparatus. Preferably, the D-rings 26 and further D-rings 28 are made of metal.

For the purposes of this disclosure, a "tight conforming fit" is defined as a fit that closely conforms to and follows the precise body plan or contours of the individual patient, including vagaries of curvature. The "tight conforming fit" may thus be considered a "skin tight" fit.

The harness/body jacket 10 may be used to achieve the requisite tight conforming fit as follows: The harness/body jacket 10 is placed on a patient. The body jacket 10 is then initially fitted on the patient as follows: The shoulder straps 12 are adjusted for fit. The jacket 14 is adjusted for fit by adjusting the front and/or back straps 36, 34 of the left and right jacket portions 13, 15 for length. The thigh extension straps 16 are then adjusted for fit (by length), and the thigh wraps 18 are adjusted for fit (by circumference). The initial fitting thus completed, the bladders 20 are inflated sufficiently to achieve the required tight conforming fit. In this manner, the harness/body jacket 10 is able to conform the vagaries of body curvature and body type, and partial weight-bearing therapy may be conducted without fear of an unwanted shift in the fit of the harness/body jacket. Additionally, in the event that the tight conforming fit is lost during the course of the therapy, the bladders can be re-inflated or deflated, as necessary to re-achieve the tight conforming fit, without having to detach the patient from the frame or other therapy apparatus or interrupting the therapy for an extended period of time.

While the invention has been described with respect to certain specific embodiments, it will be appreciated that many modifications and changes may be made by those skilled in the art without departing from the invention. It is intended, therefore, by the appended to cover all such modifications and changes as may fall within the true spirit and scope of the invention.

What is claimed is:

1. An inflatable suspension harness/body jacket for use in medical partial weight-bearing therapy, comprising:

two shoulder straps, each shoulder strap having two ends, one end of each shoulder strap passing through a central opening of a D-ring;

a jacket comprising a left jacket portion and a right jacket portion, each jacket portion having a front and a back, a top and a bottom, and inner and outer surfaces, and having a further D-ring securably attached to the bottom of the jacket portion at a point midway between the front and the back thereof;

at least one inflatable bladder securably attached to the inner surface of each of the left and right jacket portions;

a plurality of thigh extension straps, each strap having two ends;

and two thigh wraps, corresponding to a left thigh wrap and a right thigh wrap, each wrap having a front and a rear, wherein one end of each shoulder strap is securably attached to the top back of each of the left and right jacket portions, the other end of the shoulder strap being detachably attached to the top front of the same jacket portion; the left and right jacket portions are attached to each other by means of a plurality of front straps securably attached to the front of each jacket portion, and a plurality of back straps securably attached to the back of each jacket portion, with the front straps of the left jacket portion being removably attached to the front straps of the right jacket portion, and the back straps of the left jacket portion being removably attached to the back straps of the right jacket portion; one end of at least one thigh extension strap is securably attached to the front of each of the left and right jacket portions, the other end of each such thigh extension strap being securably attached to the front of one of the thigh wraps; and one end of at least one other thigh extension strap is securably attached to the back of each of the left and right jacket portions, with the other end of each such thigh extension strap being securably attached to the back of one of the thigh wraps; the thigh wraps, thigh extension straps and jacket portions being configured relative to each other such that the left thigh wrap is attached by a plurality of thigh extension straps to the left jacket portion, while the right thigh wrap is attached by another plurality of thigh extension straps to the right jacket portion; each of the D-rings being configured such that, when the suspension harness/body jacket is worn, the D-rings may be removably attached to a frame or other apparatus for offloading a portion of a patient's body weight; and each of the further D-rings being configured such that, when the suspension harness/body jacket is worn, the further D-rings also may be removably attached to the frame or other apparatus, thereby providing additional offloading capacity.

2. The inflatable suspension harness/body jacket of claim 1, wherein each of the inflatable bladders further comprises two skins, each skin having an outer surface and an inner surface, and an edge; the skins being securably attached to each other to form a hollow described by the two inner surfaces, the outer surface of one of the skins of each bladder being securably attached to the inner surface of the left or right jacket portion.

3. The inflatable suspension harness/body jacket of claim 1, wherein each of the inflatable bladders further comprises an inflation port for inflating the bladder, the inflation port including an inflation regulating valve for regulating the inflating and deflating of the bladder.

4. The inflatable suspension harness/body jacket of claim 3, wherein the inflation port further includes a hand pump for supplying air to inflate the bladder.

5. The inflatable suspension harness/body jacket of claim 1, wherein the inflatable bladders are inflated with gel or liquid or other gas.

6. A method of fitting the inflatable suspension harness/body jacket of claim 1 onto a patient to achieve a tight conforming fit thereof for partial weight-bearing therapy, comprising the following steps:

a. placing the inflatable suspension harness/body jacket on the patient;

b. initially fitting the suspension harness/body jacket, by adjusting the shoulder straps for fit, adjusting the front straps and the back straps of the left jacket portion and right jacket portion, also for fit, and adjusting the thigh extension straps and the thigh wraps, also for fit;

c. inflating the bladders sufficiently to achieve the tight conforming fit, so that the suspension harness/body jacket conforms to the shape of the patient's body, and partial weight-bearing therapy may be performed; and d. re-inflating or deflating the bladders, as necessary to re-achieve the tight conforming fit, without having to detach the patient from a frame or other therapy apparatus or interrupting the therapy for an extended period of time.

7. An inflatable suspension harness/body jacket for use in medical partial weight-bearing therapy, comprising:

two shoulder straps, each shoulder strap having two ends, one end of each shoulder strap passing through a central opening of a D-ring;

a jacket having a left side and a right side, a front and a back, a top and a bottom, and inner and outer surfaces, and having a further D-ring securably attached to the bottom of each of the left side and the right side at a point midway between the front and the back;

at least one inflatable bladder securably attached to the inner surface of the jacket;

a plurality of thigh extension straps, each strap having two ends;

and two thigh wraps, each wrap having a front and a rear, wherein one end of each shoulder strap is securably attached to the top back of each of the left and right sides of the jacket, the other end of the shoulder strap being detachably attached to the top front of the same side; one end of at least one thigh extension strap is securably attached to the front of each of the left and right sides of the jacket, the other end of each such thigh extension strap being securably attached to the front of one of the thigh wraps; and one end of at least one other thigh extension strap is securably attached to the back of each of the left and right sides of the jacket, with the other end of each such thigh extension strap being securably attached to the back of one of the thigh wraps; the thigh wraps, thigh extension straps and jacket being configured relative to each other such that one of the thigh wraps is attached by a plurality of thigh extension straps to each of the left side and right side of the jacket; each of the D-rings being configured such that, when the suspension harness/body jacket is worn, the D-rings may be removably attached to a frame or other apparatus for offloading a portion of a patient's body weight; and each of the further D-rings being configured such that, when the suspension harness/body jacket is worn, the further D-rings also may be removably attached to the frame or other apparatus, thereby providing additional offloading capacity.

8. A method of fitting the inflatable suspension harness/body jacket of claim 7 onto a patient to achieve a tight conforming fit thereof for partial weight-bearing therapy, comprising the following steps:

a. placing the inflatable suspension harness/body jacket on the patient;

b. initially fitting the suspension harness/body jacket, by adjusting the shoulder straps for fit, adjusting the jacket, also for fit, and adjusting the thigh extension straps and the thigh wraps, also for fit;

c. inflating the bladders sufficiently to achieve the tight conforming fit, so that the suspension harness/body jacket conforms to the shape of the patient's body, and partial weight-bearing therapy may be performed; and d. re-inflating or deflating the bladders, as necessary to re-achieve the tight conforming fit, without having to detach the patient from a frame or other therapy apparatus or interrupting the therapy for an extended period of time.

\* \* \* \* \*